United States Patent [19]
Vachon

[11] Patent Number: 5,531,780
[45] Date of Patent: Jul. 2, 1996

[54] IMPLANTABLE STIMULATION LEAD HAVING AN ADVANCEABLE THERAPEUTIC DRUG DELIVERY SYSTEM

[75] Inventor: David J. Vachon, Granada Hills, Calif.

[73] Assignee: Pacesetter, Inc., Sylmar, Calif.

[21] Appl. No.: 268,701

[22] Filed: Jun. 30, 1994

Related U.S. Application Data

[60] Division of Ser. No. 132,545, Oct. 6, 1993, Pat. No. 5,447,533, which is a continuation-in-part of Ser. No. 940,140, Sep. 3, 1992, abandoned.

[51] Int. Cl.[6] .................................................. A61N 1/05
[52] U.S. Cl. .................................... 607/120; 607/127
[58] Field of Search ................................ 607/115, 119, 607/120, 122, 126, 127, 128; 128/642

[56] References Cited

U.S. PATENT DOCUMENTS

| | | |
|---|---|---|
| 4,106,512 | 8/1978 | Bisping . |
| 4,146,036 | 3/1979 | Dutcher et al. . |
| 4,209,019 | 6/1980 | Dutcher et al. . |
| 4,217,913 | 8/1980 | Dutcher . |
| 4,258,724 | 3/1981 | Balat et al. ............................ 607/128 |
| 4,281,669 | 8/1981 | MacGregor . |
| 4,282,885 | 8/1981 | Bisping . |
| 4,360,031 | 11/1982 | White . |
| 4,506,680 | 3/1985 | Stokes . |
| 4,606,118 | 8/1985 | Cannon et al. ............................ 29/825 |
| 4,649,938 | 3/1987 | McArthur . |
| 4,711,251 | 12/1987 | Stokes . |
| 4,819,662 | 4/1989 | Heil, Jr. et al. . |
| 4,844,099 | 7/1989 | Skalsky et al. . |
| 4,953,564 | 9/1990 | Berthelsen ............................ 607/120 |
| 4,954,298, | 9/1990 | Yamamoto et al. . |
| 4,955,881 | 9/1990 | Eckenhoff ............................ 604/890.1 |
| 4,972,848 | 11/1990 | Di Domenico et al. . |
| 5,002,067 | 3/1991 | Berthelsen et al. ...................... 607/120 |
| 5,003,992 | 4/1991 | Holleman et al. ...................... 607/120 |
| 5,020,545 | 6/1991 | Soukup . |
| 5,324,325 | 6/1994 | Moaddeb ............................ 607/120 |

Primary Examiner—Lee S. Cohen
Assistant Examiner—Samuel Gilbert
Attorney, Agent, or Firm—Malcolm J. Romano; Harold C. Schloss

[57] ABSTRACT

A pacing lead having a stylet introduced anti-inflammatory drug delivery element advanceable from the distal tip electrode. The element is preferably formed as a moldable biocompatible composite material. The element has a biocompatible matrix material which may be combined with drugs and therapeutic agents to deliver the drugs and agents by co-dissolution or diffusion to the point of either passive or active fixation. The drug delivery element may be rigid and serve to center the means, preferably a helix, for active fixation of the lead in the myocardium.

28 Claims, 4 Drawing Sheets

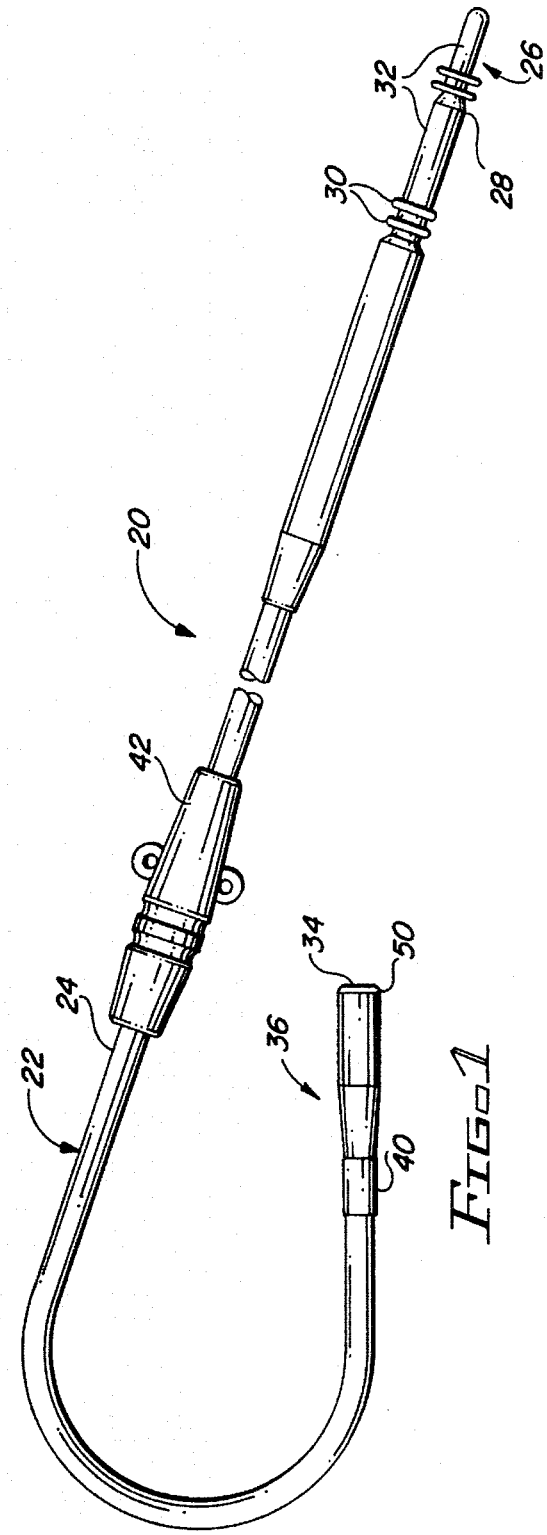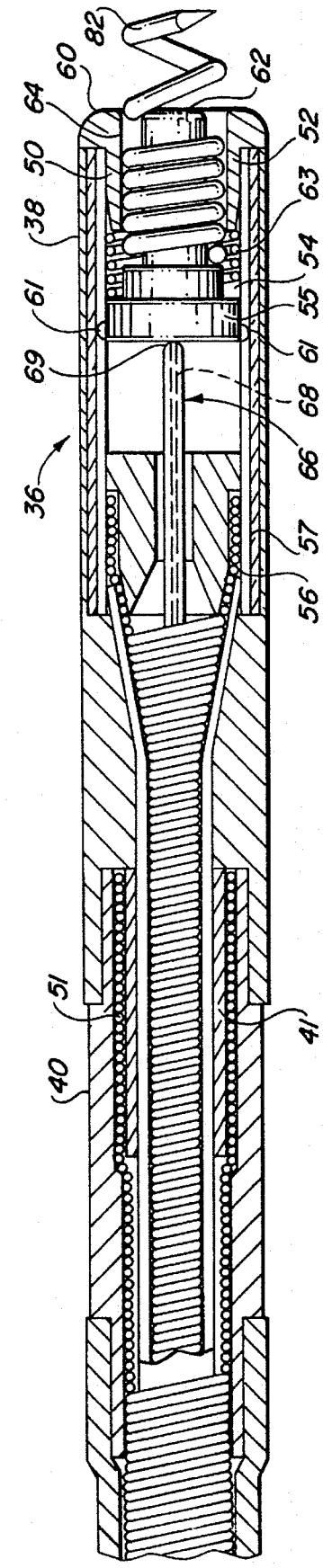

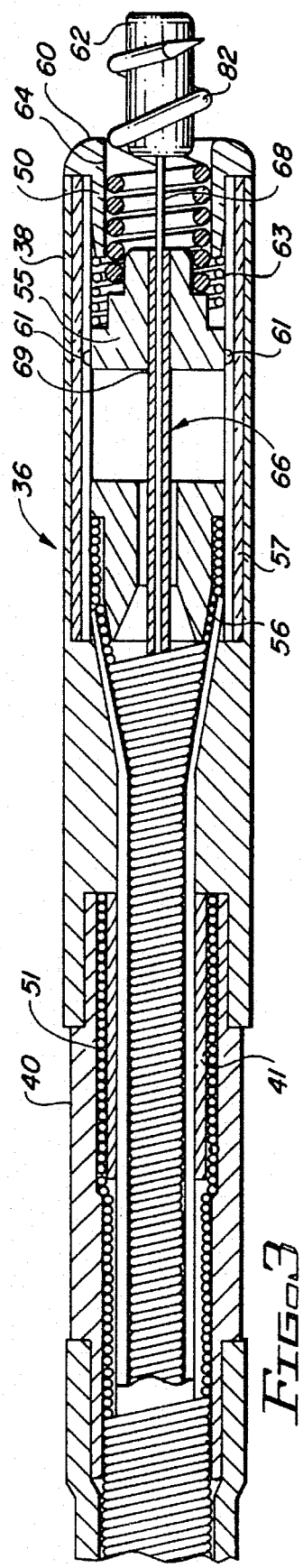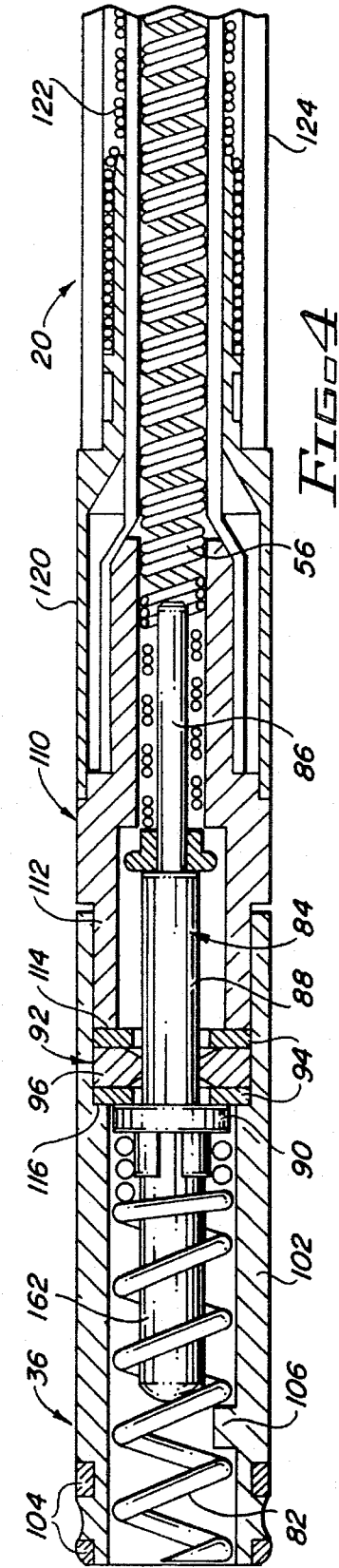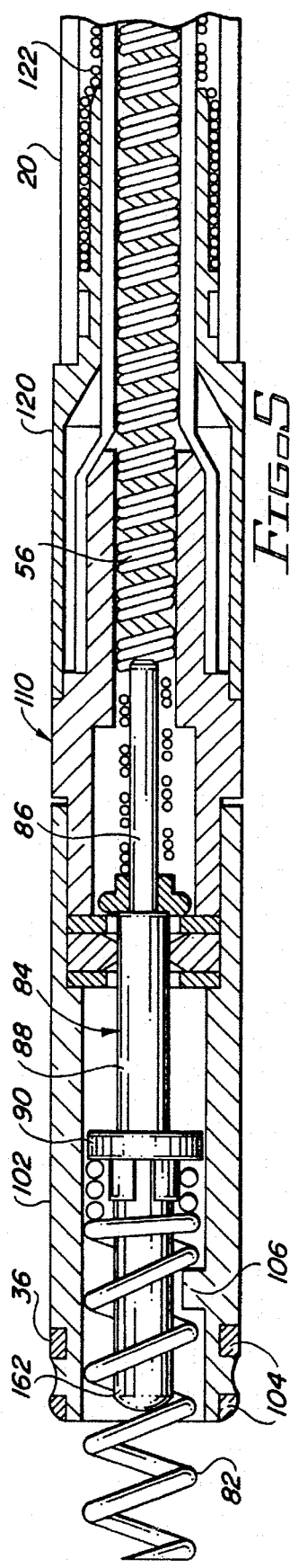

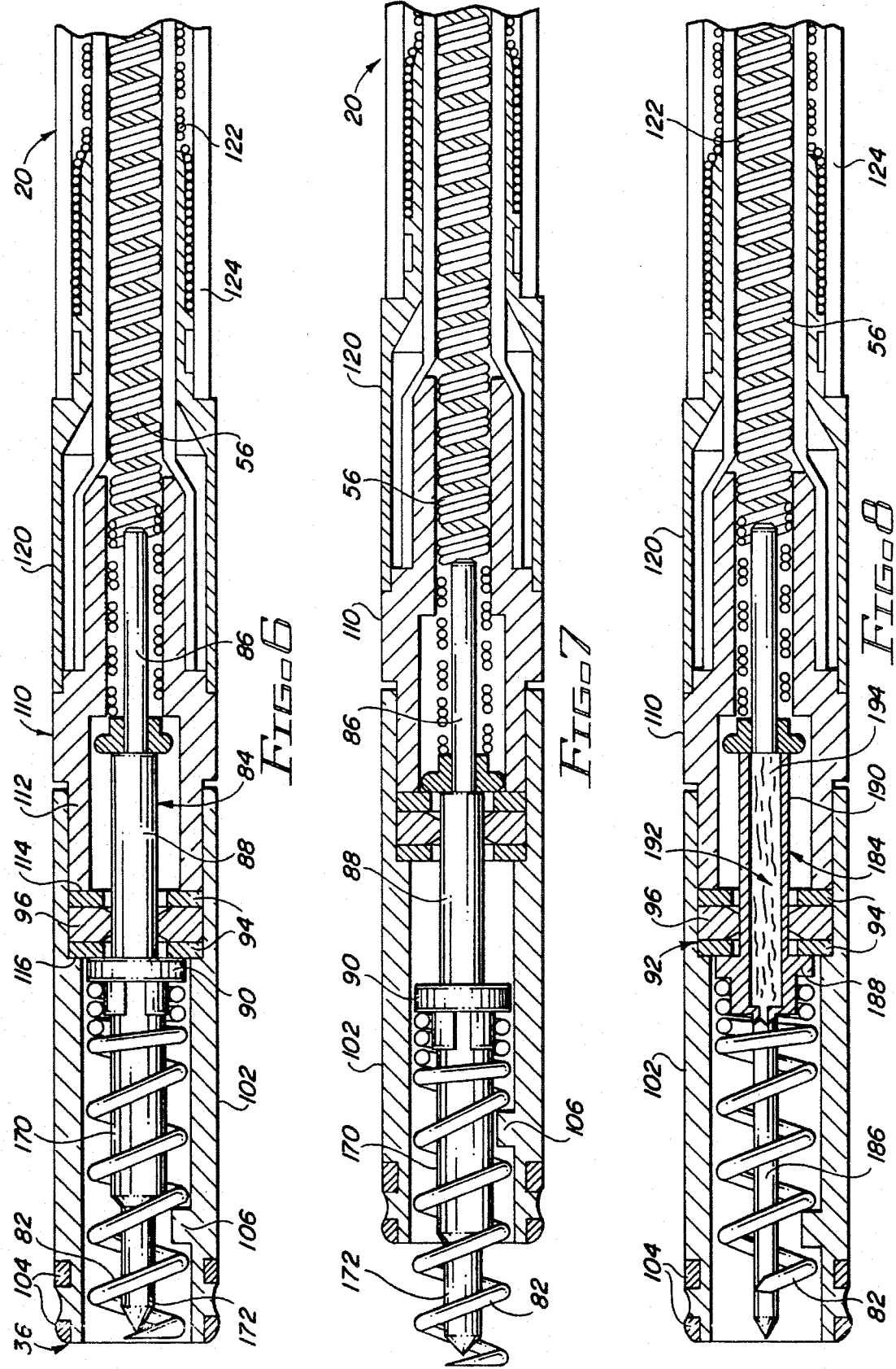

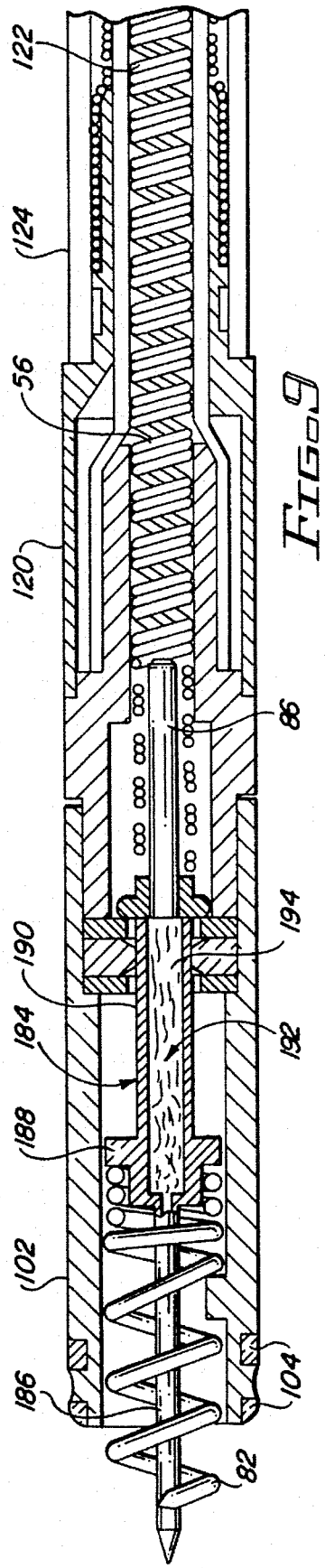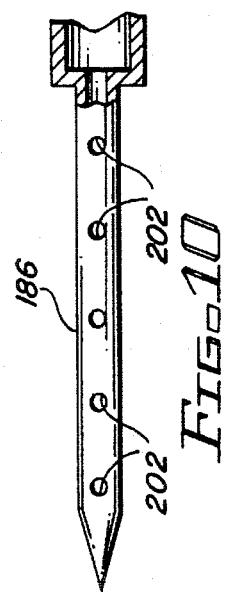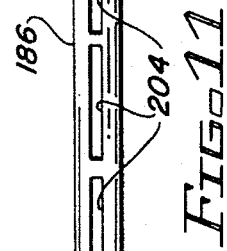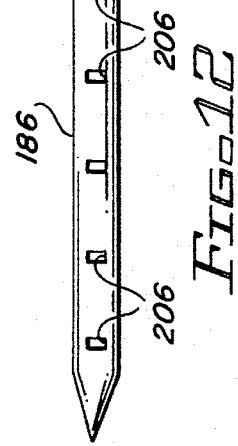

IMPLANTABLE STIMULATION LEAD HAVING AN ADVANCEABLE THERAPEUTIC DRUG DELIVERY SYSTEM

This is a divisional of copending application Ser. No. 08/132,545 filed on Oct. 6, 1993, now U.S. Pat. No. 5,447,533, which is a continuation-in-part of copending application Ser. No. 07/940,140, filed Sep. 3, 1992, abandoned.

FIELD OF THE INVENTION

This invention relates generally to an implantable stimulation lead for use with an implantable pulse generator such as a cardiac pacemaker. More specifically, the invention relates to an implantable stimulation lead having an anti-inflammatory drug delivery system at the distal tip electrode. In a preferred embodiment of the invention, the drug delivery system may serve to center or anchor the lead at a desired site when the lead is fixated in the heart. In a preferred embodiment of the invention, the drug delivery system may serve to center or anchor the lead at a desired site when the lead is being fixated in the heart.

BACKGROUND OF THE INVENTION

For a cardiac pacemaker, functional implant life time is, in part, determined by the energy delivered per pulse. The pacemaker will have a longer life if the energy delivered per pulse can be maintained at a minimum. The design of an implantable pacing lead which is used with the pacemaker is influenced by the electrical signal required for pacing stimulation. Preferably, a key design objective for a pacing lead should be the maximization of stimulation energy with minimum battery current drain over the life of the pacemaker. These objectives therefor require considerations of the lead's electrode design, geometry, and pacing threshold minimization.

Generally, pacing leads have utilized electrically conductive metals such as a platinum, platinum-iridium, or carbon composition for the tip electrode. Physiologically, a cardiac pacemaker must be capable of generating a signal with a sufficient magnitude to depolarize the excitable cells of the myocardium to initiate contraction. The electrode shape, size, surface nature, and material; the body fluid or electrolyte conductivity; and the distance separating the electrode and the excitable cardiac tissue, combine to determine the energy required of the pacemaker. Thus, the main factors to be considered with regard to the design of an implantable stimulation lead are: shape, size, surface nature, materials, fixation of the electrode, and the cardiac tissue reaction.

The pacing or stimulation threshold is a reflection of the energy required for a pulse to initiate and maintain consistent cardiac contractions. When a lead is implanted, the stimulation threshold generally is at a relatively low level and then rises for a period of a few weeks after the implant of the lead. The typical rise in the threshold has been believed to be a result of an increase in the spacing between the electrode and the excitable cardiac tissue. It is generally believed that the spacing increase occurs primarily due to the inflammatory response and the subsequent development of a fibrous capsule around the electrode tip.

One factor which influences the development of the fibrous capsule is the constant beating of the heart, which causes the electrode to pound against the endocardium, causing irritation. Additionally, any rough surface structure of the electrode tip may be abrasive on the abutting tissue, causing still further irritation. The irritation of the endocardial tissue, as well as the patient's natural foreign body reaction to the presence of the electrode, results in the initiation of the inflammatory response and the subsequent fibrous capsule development. The fibrous capsule increases in thickness in an attempt by the body to wall-off the foreign material. Thus, thickness of the fibrous capsule is also dependent upon the geometry, materials, and structure of the electrode tip, and the foreign body reaction process.

In order to counter, delay or suppress the occurrence of the inflammatory response and therefore the growth of the fibrous capsule, pacing leads have been developed which include a drug or steroid-eluting tip electrode structure. Examples of these types of leads include U.S. Pat. Nos. 4,606,118 (Cannon et al.); 4,711,251 (Stokes); 4,844,099 (Skalsky et al.); and 4,953,564 (Berthelsen). These patents generally detail implantable leads which include a reservoir which is located typically within the tip electrode structure proximate to the distal tip electrode. The drugs are usually dispensed through a porous media of the tip electrode. Typically, the drug is intended to counter thrombus formation, fibrosis, inflammation or arrhythmias, or any combination thereof.

As alternative designs, the '251 patent depicts a sintered electrode material having a high surface area on which the drug to be dispensed is deposited in a solid form as a coating. A solid composite material including the drug may also be employed to form the sheath and/or the tines of the electrode.

Further, U.S. Pat. No. 4,953,564 discloses an active fixation pacing lead having an extendable fixation helix and a controlled release device advanceable with the helix. In this patent, therapeutic drugs are contained in the controlled release device, which is itself encased in a housing having a porous eluting path for the therapeutic agent to traverse.

These designs for pacing leads attempt to reduce and delaying the growth of the fibrous capsule. However their effectiveness is limited by the requirement of having the drugs enclosed within the reservoir or encasement from which they must escape via the porous eluting path. In addition, the drug delivery in each of the above patents is introduced at the electrode surface to the inner wall of the myocardium. Following initial implant, a substantial portion of the therapeutic material can be washed away or dissipated into the blood pumping through the heart, and is therefore wasted.

In view of the above characteristics of an electrode for a cardiac pacemaker, minimal tissue reaction is desired around the tip, but high electrical coupling of the electrode to the tissue is essential. An electrode for a pacing lead which satisfies both of these criteria, and which also has the ability to deliver specific drugs directly to the endocardial tissue, is therefore highly desirable.

SUMMARY OF THE INVENTION

The present invention is directed to an implantable pacing lead having an active fixation electrode for use with a cardiac pacemaker, which has a stylet introduced, anti-inflammatory drug delivery system. The drug delivery system preferably comprises a dart which is formed from a biocompatible, composite material. The dart is preferably capable of penetrating the myocardial wall. The dart preferably includes a drug carried in a bioabsorbable, polymeric matrix which optimally has an innate hypo-inflammatory property. Preferred matrix materials for the dart include polyglycolic acid, polylactic acid, copolymers of lactic/ glycolic acids, polyesters, polyorthoesters, polyanhydrides and polyamino acids. Suitable dart materials also include proteins, such as albumin, collagen and gelatin preferably in their crosslinked forms. These materials may be combined with drugs and therapeutic agents to allow delivery of the drugs and agents by co-dissolution, diffusion or resorption. The pacing lead includes an advanceable helix or cork screw type active fixation means, and the stylet introduced drug delivery system is introduced coaxially with respect to the active fixation means. In one embodiment the dart may be a rigid material, including a pin, which extends beyond the helix tip, for penetrating the myocardium first to thereby center the helix as the helix is being fixated in the myocardium.

DESCRIPTION OF THE DRAWINGS

FIG. 1 shows a side plan view of a pacing lead according to the present invention.

FIG. 2 shows a partial cross-sectional view of the distal tip of the electrode of the lead of FIG. 1 with the therapeutic delivering dart in the retracted position.

FIG. 3 shows an enlarged partial cross-sectional view of the distal tip of the electrode of the lead of FIG. 1 with the therapeutic delivery dart in the extended position.

FIG. 4 shows an enlarged partial cross-sectional view of an alternative embodiment for the distal tip of the electrode of the lead of FIG. 1 with the fixation helical electrode in the retracted position.

FIG. 5 shows an enlarged partial cross-sectional view of an alternative embodiment for the distal tip of the electrode of the lead of FIG. 1 with the fixation helical electrode in the extended position.

FIG. 6 shows an enlarged partial cross-sectional view of a second alternate embodiment of the present invention with the fixation helix electrode in the retracted position.

FIG. 7 shows an enlarged partial cross-sectional view of a second alternate embodiment of the present invention with the fixation helix electrode in the extended position.

FIG. 8 shows an enlarged partial cross-sectional view of a third alternative embodiment of the present invention with the fixation helix electrode in the retracted position.

FIG. 9 shows an enlarged partial cross-sectional view of a third alternative embodiment of the present invention with the fixation helix electrode in the extended position.

FIGS. 10, 11 and 12 depict enlarged views of alternative syringe designs for use with the embodiments of FIGS. 8 and 9.

DETAILED DESCRIPTION OF THE PREFERRED EMBODIMENT

FIG. 1 shows a side plan view of a pacing lead 20 according to the present invention. The lead 20 is designed for intravenous insertion and contact with the endocardium, and as such, may be conventionally referred to as an endocardial lead. The lead 20 is designed for intravenous insertion and contact with the endocardium and, as such, may be conventionally referred to as an endocardial lead. The lead 20 is provided with an elongated lead body 22 which includes coil or helically wound electrical conductors (not shown) covered with an insulation sheath 24. The insulation sheath is preferably fabricated of silicone rubber, polyurethane or other suitable plastic. At a proximal end 26 of the pacing lead 20 is a connector assembly 28, which is provided with sealing rings 30, and which carries at least one, and preferably a couple of electrical connectors 32.

The connector assembly 28 is constructed using known techniques and is preferably fabricated of silicone rubber, polyurethane or other suitable plastic. Connectors 32 are preferably fabricated of stainless steel or other suitable electrically conductive material. The lead 20 is constructed to include a hollow interior extending from the proximal end 26 to a distal end 34. The hollow interior allows for the introduction of a stylet during implant, which is beneficial in allowing the surgeon to guide the otherwise flexible lead 20 from the point of venous insertion to the myocardium.

At the distal end 34 of the pacing lead 20 is an electrode assembly 36 which is discussed in more detail below. A fixation sleeve 42, slidably mounted around lead body 22, serves to stabilize the pacing lead 20 at the site of venous insertion.

The electrode assembly 36 of FIG. 1 is shown in greater cross-sectional detail in FIG. 2 (the base 55 and helix 82 not in cross-section) and FIG. 3 (the helix portion extending beyond the distal end 34 not in cross-section). As illustrated, the electrode assembly 36 includes a conductive electrode 50 and located about the distal end 34 of the electrode assembly 36 is an insulating sheath 38 which extends from the distal end of lead body 22 to an annular ring electrode 40.

Lead conductor 51 is crimped to crimp tube 41, which is in electrical contact with ring electrode 40, thereby establishing an electrical connection between conductor 51 and electrode 40.

The conductive electrode 50 is preferably a unitary construction including at its proximal end, a cylindrical portion 52 being secured by means of a press fit in an axial bore 54 that is defined by conductive annular sleeve 57. The helical coil conductor 56 extends through the lead body 22 of FIG. 1, and is electrically coupled, typically by way of crimping, to the annular sleeve 57. The sleeve 57 extends substantially to the distal end 34 where, as just described, electrical contact is therefore made with electrode 50. As illustrated, the helical coil conductor 56 defines the walls of the hollow interior of the pacing lead 20, which accepts a stylet 66 during insertion. Stylet 66 may be coaxial containing plunger 68 which is extendable beyond the distal end 69 of the stylet.

Located in bore 54 is base 55 which is longitudinally slidable within bore 54 under the action of stylet 66. A pair of opposite facing grooves 59 extend substantially the length of the inner surface of annular sleeve 57 and within which tabs 61, which depend from base 55, extend. Accordingly, the interaction of the tabs 61 and grooves 59 provides for translational movement while inhibiting rotational movement of base 55 relative to electrode assembly 36.

Located between base 55 and electrode 50 is a helical spring 63 which compresses under the action of stylet 66 such that when stylet 66 urges base 55 toward the distal end of lead body 22, helical spring 63 compresses and thereby causes the base 55 to move back away from the distal end when the force applied by stylet 66 is released.

The electrode distal tip 60 is depicted as including an internal bore 64 defined by the inner annular surface of conductive electrode 50.

The electrode materials for the electrode distal tip 60 are preferably a base metallic material, optimally a platinum-iridium alloy or similarly conductive biocompatible material. In the preferred embodiment, the platinum-iridium alloy has a composition of about 90% platinum and 10% iridium by weight. Disposed within the internal bore 64 is a therapeutic delivery means such as an axially movable, therapeutic agent delivering dart 62. The electrode distal tip 60 also includes a fixation helix electrode 82 which is mounted on base 55, typically by laser welding, and centrally disposed with respect to the distal tip 60. The fixation helix electrode 82 is extendable from within the internal bore 64 when the stylet 66 is urged against base 55. As previously described, when the stylet 66 is retracted, the helix will also retract under the reaction of helical spring 63.

The dart 62 is axially movable in response to the surgeons use of the stylet during implantation. In one embodiment, following fixation of the helix electrode 82 within the myocardium, the dart 62 is advanced through the internal bore 64 by manipulation of the stylet until the dart engages the myocardial tissue. This may be facilitated by the use, for example, of a coaxial stylet having an inner wire 68 which is extendable beyond the distal end of stylet 66 and through a bore 70 in base 55 to thereby contact the dart 62 and drive it into the myocardial tissue. In another embodiment, the dart 62 may be mounted on base 55 so that it moves only to the same extent as does the helix 82. There are several methods to maintain the dart 62 in place prior to being driven into the myocardial tissue. For example, the dart 62 may be cylindrical, having a diameter slightly larger than the inside diameter of the helix 82, whereby a friction fit is established between the dart 62 and the helix 82 providing sufficient retention of the dart 62 while permitting the dart 62 to be driven into the myocardial tissue merely under the action of inner wire 68. The dart 62 may also be configured so as to provide active fixation of the dart 62 to the myocardial tissue, as discussed in greater detail below.

In FIG. 3, the dart 62 is illustrated in the extended position, i.e., it has been forced through the helix 82 by inner wire 68. Preferably, the stylet 66 has an opening (not shown) at its distal end to permit the inner wire 68 to extend beyond the stylet's distal end 69. By this arrangement, the stylet 66 is designed to be relatively rigid to aid implantation of the pacing lead 20, while the inner wire 68 can be advanced through the stylet 66 to abut against and forcibly advance the dart 62.

As priorly noted by virtue of the engagement of tabs 61 in longitudinal grooves 59, the base 55 and therefore helix 82 is prevented from rotational motion relative to electrode assembly 36. Thus, in order to rotate the helix 82 into myocardial tissue, the entire lead body 22 must be rotated while the helix is in the extended position.

FIGS. 4 and 5 depict a first alternative embodiment for the distal end 36 of the pacing lead 20 of FIG. 1. In FIGS. 4 and 5 the helical electrode 82 is affixed to an advanceable electrical interconnect 84. The electrical interconnect 84 is also electrically connected to the conductor 56 which extends from the distal to the proximal end of the pacing lead 20. The electrical interconnect 84 thus includes a tail portion 86, to which the conductor 56 is secured, a central shaft portion 88 and a head portion 90. The helical electrode 82 is connected to the head portion 90. The shaft portion 88 of electrical interconnect passes through a seal assembly 92. The seal assembly 92 may include a pair of retaining rings 94 which cooperate to secure a resilient ring seal 96. The seal assembly 92 prevents bodily fluids from penetrating into the axial void extending through the center of the pacing lead 20.

As also depicted in FIGS. 4 and 5, the distal end 36 of the pacing lead 20 terminates in a sleeve 102 which is essentially a cylindrical element having a central bore within which the helical electrode 82 is disposed and retractable. The sleeve 102 is preferably fabricated from a biocompatible elastomeric material. The distal tip of sleeve 102 may include one or more metallic rings 104, which are useful during implant to allow a physician to view the placement of the distal tip 36 by the use of a fluoroscope. Further, the sleeve 102 includes a knob 106 extending from the inner diameter to guide the rotative advancement of the helical electrode 82. It is to be understood that techniques for implanting a pacing lead and advancing the fixation elements are known in the art, and, therefore, will not be discussed herein.

The proximal end of the sleeve 102 is affixed to a stepped cylindrical element 110, which is preferably formed from a biocompatible nonconductive material. The stepped cylindrical element 110 includes a cylindrical portion 112 which slides into the proximal end of the cylindrical sleeve 102 and is bonded thereto. The seal assembly 92 is located between an end-face 114 of the step cylindrical element 110 and an internal step 116 of the sleeve 102.

As further illustrated in FIGS. 4 and 5, the proximal end 36 of the pacing lead 20 may include a second ring electrode or sensor electrode 120 spaced proximally of the distal tip. The ring electrode 120 is electrically interconnected to a second conductor 122 which also extends from the proximal to the distal end of the lead body 22 and is helically wrapped about the cylindrical insulation containing the first conductor 56. The second electrical conductor 122 is also preferably encased in an insulation sleeve 124. The second electrical conductor 122 extends to and interconnects with an electrical contact (not shown) located at the connector assembly 28 at the proximal end 26 of the pacing lead 20.

In FIGS. 4 and 5, the therapeutic delivery means is a therapeutic bullet 162 centrally disposed with respect to the helical electrode 82, i.e., along the axis of the helix. The therapeutic bullet 162 is preferably secured to the head portion 90 of the electrical interconnect 84, and advanceable therewith. As depicted in FIG. 5, when the helical electrode 82 is fully extended and inserted into the myocardium upon implant, the therapeutic bullet 162 does not extend out of the end of the sleeve 102 as does the helical electrode 82. The construction of the therapeutic bullet 162 is described in detail below. Unlike the design illustrated in FIGS. 2 and 3, the therapeutic bullet 162 of FIGS. 4 and 5 is only advanceable with the advancement of the electrical interconnect 84, and is not independently advanceable.

FIGS. 6 and 7 depict a second alternative embodiment for the distal end 36 of the pacing lead 20 of FIG. 1. In FIGS. 6 and 7, a majority of the same elements discussed above with respect to FIGS. 4 and 5 are also included. The difference in the embodiment of FIGS. 6 and 7 is that the therapeutic delivery means is a therapeutic element 170, which includes a tapered and pointed projection 172, which coaxially aligns with the helical electrode 82, and which terminates at a point proximate the end of the helical electrode 82. Thus, as the helical electrode 82 is advanced to penetrate the myocardium, the projection 172 of therapeutic element 170 also advances to penetrate the myocardium, as illustrated in FIG. 7. The advantage derived from the use of the pointed therapeutic element 170 is that the therapeutic drugs are delivered to a location proximate the implanted tip of the helical electrode 82, i.e. close to the site of tissue damage. Thus, the therapeutic element 170 is designed to be partially advanced into the myocardial tissue. In comparison to prior designs, the therapeutic drugs are delivered directly into the muscle of the myocardium proximate the areas of injury caused by the advancement of the helical electrode 82.

The therapeutic element 170 is fabricated from a material which possesses the mechanical properties required to pierce the tissue yet is resorbed by the body over time. The therapeutic element 170 of FIGS. 6 and 7, as well as the therapeutic bullet 162 of FIGS. 4 and 5 and the dart 62 of FIG. 3, are preferably compounded from a mixture of copolymeric Lactic/Glycolic acid (PLA/GLA), polylactic acid, polyglycolic acid, polyamino acid, or polyorthoester and a desirable therapeutic, up to 50% by weight, such as dexamethasone sodium phosphate for the minimization of inflammation resultant from foreign body reactions to the surrounding tissue. The dart or elements release the desired therapy over time to counter the commonly known undesirable side effects of the implant, ie. inflammation. Because the dart or elements are at the center of the helical electrode 82 they can deliver the therapy to the myocardium, very close to the site of implantation of the helical electrode 82.

Resorption of the therapeutic element 170 material is beneficial due to the fact that the foreign body reaction is minimized as a result of the surface erosion. It is this erosion which inhibits the inflammatory components (macrophages, foreign body giant cells, etc.) from adhering to the surface thus resulting in a decreased response. When the drug is compounded into such an eroding component the benefit is even greater.

The therapeutic delivery means, such as dart 62, therapeutic bullet 162 or therapeutic element 170 may be formed by a molding or casting process, for example, to have the desired shapes. The materials for the dart 62 are selected to provide an anti-inflammatory media at the tip 60 which is in contact with the endocardial tissue. The dart 62 provides a means for delivering drugs or therapeutic agents by resorption, co-dissolution or diffusion. Accordingly, the dart 62 is preferably a composition of a matrix material and an anti-inflammatory agent or drug. Significantly, the entire dart 62 is formed from the composite material. For a dart 62 which includes a dissolving matrix material, when the drug and matrix materials are dissipated, there is no foreign body remaining in the space previously occupied by the dart 62.

There are several considerations which must be addressed when choosing the constituents of the dart 62. The most important criteria are: (1) the dart 62 should have sufficient structural integrity to allow manipulation within the internal bore 64; (2) the dart 62 must not adversely affect the ability of the electrode to deliver a stimulus to the cardiac tissue; and (3) the dart 62 must allow for the delivery of some therapeutic agent by co-dissolution or diffusion. Additionally, the matrix material for the dart 62 may possess inherent hypo-inflammatory properties. Thus, the dart 62, whether oligomeric, polymeric or monomeric, must not interfere with the ability of the conductive electrode 50 to deliver a stimulus while delivering the anti-inflammatory drug or therapeutic agent directly to the cardiac tissue.

The dart 62 must exhibit a high degree of biocompatibility, such that it will not initiate an aggressive foreign body response upon implantation. Both hydrophilic and hydrophobic materials may be employed, as long as they demonstrate biocompatibility. Polymeric systems selected from the group including polylactic acid, polyglycolic acid, polyorthoesters, polyesters, polyurethanes, polyamino acids, lactic/glycolic acid copolymers (or PLA/GLA copolymers), polyamino acids, such as polylysine, polyanhydrides and ion exchange resins, such as sulfonated polytetrafluoroethylene (as sold under the name NAFION, manufactured by DuPont), are suitable matrix materials for the dart 62.

Suitable dart materials also include crosslinked proteins, such as albumin, collagen and gelatin. Crosslinking agents, such as 1-ethyl-3-(3-Dimethylamino-propyl)carbodiimide hydrochloride are quite effective at carrying out the crosslinking reaction while allowing for easy removable of by-product and excess reagent by washing with water or diluted acid. These matrix materials can deliver therapeutic agents by co-dissolution or surface erosion due to resorption, or degradation of the polymer matrix (due to hydrolysis of the matrix).

For any of the above types of matrix materials for the dart 62, the composition of the matrix material with the therapeutic agent discussed below should have a solid physical property. Thus, the composition should be sufficiently rigid to allow forcible insertion. Accordingly, the composition for the dart 62 should have a structural rigidity in the range of between 50A Shore hardness to 95D Shore hardness.

The dart 62 is preferably a mixture of one of the above matrix materials blended with an anti-inflammatory agent selected from the group including fluoro-trihydroxy-methyl pregna diene/dione or fluoro-methylprednisolone, sodium phosphate, the sodium salt of methoxy-methyl-naphthalene-acetic-acid, sodium, or the sodium salt of isobutylphenyl-propionic acid. Other anti-inflammatory or therapeutic agents compatible with the particular matrix material may also be utilized to form the dart 62. Preferably, the anti-inflammatory agents constitute between about 0.01% to 50% by weight of the dart 62, within the matrix material comprising the remainder. The therapeutic content can be increased as long as the mechanical properties of the dart are not compromised.

It is important to note that with many therapeutic agents, the solubility can be manipulated by controlling ionic character. As an example, methoxy-methyl-naphthalene-acetic-acid, an anti-inflammatory agent containing a carboxylic acid moiety is quite insoluble in aqueous media in the acid form. However, upon an increase in pH the acid can be converted to the conjugate base or salt form rendering it soluble in aqueous media. In the case of an anti-inflammatory agent such as the sodium salt of methoxy-methyl-naphthalene-acetic-acid, the agent becomes freely soluble. These two forms of the anti-inflammatory exhibit a similar anti-inflammatory responses in humans. When both forms are blended together into a polymer matrix which swells upon exposure to physiologic fluids, these two forms demonstrate different rates of dissolution or diffusion from the matrix. Thus, release rates of the anti-inflammatory agent from a variety of matrices can be manipulated by varying the therapeutic agent pH, matrix morphology, and the matrix material of choice.

In an alternative embodiment, the dart 62 includes at least one anti-inflammatory agent carried in the matrix material, and the agent is itself a mixture of at least two different chemical forms of the agent having at least two different rates of dissolution or diffusion. One example of a method of accomplishing this preferred embodiment is to use a blend of fifty percent methoxy-methyl-naphthalene-acetic-acid and fifty percent sodium salt of methoxy-methyl-naphthalene-acetic-acid. As can readily be appreciated, the relative percentages of these forms of the anti-inflammatory agent can be varied to cause the agent to be consumed at a faster or slower rate, as desired.

In the foregoing discussion of the materials and physical properties of the dart 62, it is to be understood that the discussion is equally applicable to the therapeutic bullet 162, and therapeutic element 170 of FIGS. 4–7.

FIGS. 8 and 9 depict a third alternative embodiment for the distal end 36 of the present invention. The embodiment illustrated in FIGS. 8 and 9 include a number of elements common to those detailed above with respect to FIGS. 4 through 7. For the following description of FIGS. 8 and 9, if the elements have not change from the description above in FIG. 4, then the reference numbers remain the same.

One difference of the embodiment illustrated in FIGS. 8 and 9 is the design of the electrical interconnect 184 and the use of an intrahelix syringe 186 which combine to form the therapeutic delivery means. The intrahelix syringe 186 is coaxially disposed with respect to the helical electrode 82. The intrahelix syringe 186 has an axial bore extending along its axis, and is interconnected at its distal end to the head portion 188 of the electrical interconnect 184. The electrical interconnect 184 includes a hollow central body 190 defining a chamber 192 which is filled with a flowable therapeutic compound 194. The chamber 192 is in open communication with the axial bore extending through the center of the syringe 186, thereby allowing the therapeutic compound 194 to elute through the intrahelix syringe 186 into the myocardium. The syringe 186 is advanceable with the helical electrode 182, such that the tip of the syringe 186 advances a distance approximately equal to the distance advanced by the helical electrode 182.

As the helical electrode 82 engages tissue, the intrahelix syringe 186 is inserted into the tissue at the center of the helical electrode 82. The chamber 192 is loaded with a therapeutic compound 194 such as dexamethasone sodium phosphate, preferably in a form so as to allow it to flow toward the intrahelix syringe 186. The intrahelix syringe 186 may have more than one exit port 202 in order to allow elusion of therapeutic compound 194 to various sites. In a preferred embodiment, the therapeutic compound 194 is one that has a temperature dependant viscosity. Thus, prior to implant the therapeutic compound 194 is a solid or semi-solid. However, after implant and equilibration to body temperature (about 37° C.) the therapeutic compound 194 will become more viscous and flow with gravity. Thus, Polysorbate 80 (Tween 80-ICI) or z-sorbitan mono-9-octa-decanote poly (oxy-1-2-ethanediyl) when combined with an aqueous dexamethasone sodium phosphate solution display the low flow characteristics at room temperature and high flow characteristics at body temperature, normally about 37° C.

Another difference of the embodiment illustrated in FIGS. 8 and 9 is the form of the intrahelix syringe 186, which extends essentially coaxially through the fixation helix electrode 82. The syringe 186 may be in the form of a thin pin, either solid or containing a lumen or a plurality of small holes, or in a form similar to the therapeutic element 170 previously described, as well as being similar to the embodiments shown in FIGS. 10 through 12 as described below.

Preferably, the syringe 186 extends beyond the distal extremity of the fixation helix electrode 82 and therefore is first to penetrate the myocardium at a desired site. When the fixation helix electrode 82 is to be fixated in the myocardium, the first entrance of the syringe 186 into the myocardium serves to define a substantially fixed axis about which the fixation helix electrode 82 is to be rotated (screwed) into the myocardium. Accordingly, the location of the distal tip 36 is stabilized by minimizing the potential of the distal tip 36 from "jumping" or meandering away from the site, as the fixation helix electrode 82 is screwed into the myocardium. Although the syringe 186 extends beyond the distal extremity of the fixation helix electrode 82, in the retracted position, the distal end of syringe 186 is contained within the sleeve 102.

Additionally, when the syringe 86 is formed of electrically conductive material, such as a metal, it may also serve as an active electrode and the ability to position the syringe 86 into the cardiac tissue without affixing the fixation helix electrode 82, can greatly aid in "mapping" the endocardial surface prior to fixation. Techniques for providing electrical connections to the syringe 186 and performing "mapping" are well known in the art.

FIGS. 10 through 12 depict further alternative embodiments for the syringe 186 of FIGS. 8 and 9. In FIG. 10, the syringe 186 includes a plurality of laser drilled ports 202 spaced behind the distal tip of the syringe 186. The laser drilled ports 202 allow the flowable therapeutic compound 194 to elute to specific locations, thereby providing the therapeutic drug delivery to either or both of the myocardial wall and to the myocardial muscle. In FIG. 11, the ports 202 of syringe 186 of FIG. 10 are replaced with vertical slots 204. In the third embodiment for the syringe 186 shown in FIG. 12, the ports 202 of FIG. 10 are replaced with horizontal slots 206. The vertical slots 204 or horizontal slots 206, of FIGS. 11 and 12 respectively, as well as the ports 202 of FIG. 10, may be formed by a number of processes, including machining, laser drilling and electrochemical machining. It may also be noted that the number and location of the ports 202, vertical slots 204 or horizontal slots 206 can be tailored for specific applications, such that they may be located only proximate the distal tip to deliver the therapeutic drug only submyocardially, or they may extend the length of the syringe 186 to allow elusion of the therapeutic drug at discreet points along the entire length of the syringe 186.

It is also contemplated that the ports 202 or slots 204, 206, in addition to the opening at the tip of the syringe 186, may be sealed with a bioabsorbable material to contain the therapeutic compound in the chamber 192 during the initial implant of the lead 20. Thus, following implant and insertion of the helical electrode 182 and the syringe 186, the bioabsorbable material plugging the elution path would be absorbed, and the therapeutic compound would then commence eluting to the myocardial tissue.

It should be evident from the foregoing description that the present invention provides many advantages over pacing leads of the prior art. Although preferred embodiments are specifically illustrated herein, it will be appreciated to those skilled in the art that many modifications and variations of the present invention are possible. It is therefore preferred that the present invention be limited only by the proper scope of the appended claims.

What is claimed is:

1. An implantable pacing lead for use with a cardiac pacemaker, said pacing lead comprising:

an electrical conductor having a proximal end and a distal end;

an insulation sheath encasing said electrical conductor;

an electrical connector affixed to said proximal end of said conductor;

an active fixation electrode assembly affixed to said distal end of said conductor, said electrode assembly having a helical electrode capable of axial advancement outward relative to said distal end for penetrating into myocardial tissue; and therapeutic delivery means for delivering a therapeutic compound, axially advanceable outward relative to said distal end along an axis of the helical electrode simultaneously with the advancing of said active fixation electrode assembly, said therapeutic delivery means comprising intrahelix means for penetrating myocardial tissue at a center of the helical electrode.

2. The pacing lead of claim 1, wherein said therapeutic delivery means further comprises a therapeutic eluting reservoir.

3. The pacing lead of claim 2, wherein said therapeutic eluting reservoir contains a therapeutic solution having a temperature dependant flow property, said therapeutic solution for preventing inflammation of said myocardial tissue.

4. The pacing lead of claim 3, wherein said therapeutic solution includes dexamethasone sodium phosphate.

5. The pacing lead of claim 3, wherein said therapeutic solution includes Polysorbate 80.

6. The pacing lead of claim 1, wherein said therapeutic delivery means has a plurality of therapeutic eluting openings.

7. The pacing lead of claim 6, wherein said therapeutic eluting openings comprise ports.

8. The pacing lead of claim 6, wherein said therapeutic eluting openings comprise vertical slots.

9. The pacing lead of claim 6, wherein said therapeutic eluting openings comprise horizontal slots.

10. The pacing lead of claim 6, wherein said therapeutic delivery means further comprises means for sealing said therapeutic eluting openings.

11. The pacing lead of claim 10, wherein said means for sealing comprises a bioabsorbable material.

12. The pacing lead of claim 6, wherein said therapeutic delivery means further comprises a therapeutic eluting reservoir in fluid communication with said plurality of therapeutic eluting openings.

13. The pacing lead of claim 1, wherein said means for penetrating myocardial tissue comprises a solid thin pin.

14. The pacing lead of claim 1, wherein said means for penetrating myocardial tissue comprises a thin pin having a lumen.

15. The pacing lead of claim 1, wherein said means for penetrating myocardial tissue comprises an electrically conductive material and wherein said means for penetrating myocardial tissue is electrically connected to said electrical conductor.

16. The pacing lead of claim 1, wherein said therapeutic delivery means further comprises a formable rigid composition of a biocompatible matrix material.

17. The pacing lead of claim 16, wherein said biocompatible matrix material is a material selected from the group consisting of polylactic acid, polyglycolic acid, polylactic/glycolic acid copolymers, polyorthoesters, polyesters, polyurethanes, polyanhydrides, polyamino acids and ion exchange resins.

18. The pacing lead of claim 17, wherein said ion exchange resin is sulfonated polytetrafluoroethylene.

19. The pacing lead of claim 16, wherein said biocompatible matrix material is a material selected from the group of proteins consisting of collagen, gelatin, and albumin.

20. The pacing lead of claim 1, wherein said therapeutic delivery means further comprises a therapeutic agent.

21. The pacing lead of claim 20, wherein said therapeutic agent is selected from the group consisting of fluoro-trihydroxyl-methyl pregna diene/dione, fluoro-methylprednisolone, sodium phosphate, a sodium salt of methoxy-methyl-napthalene-acetic-acid, sodium, and a sodium salt of isobutylphenyl-propionic acid.

22. The pacing lead of claim 20, wherein said therapy delivery means includes a mixture of at least two different forms of said therapeutic agent which have different rates of dissolution or diffusion.

23. The pacing lead of claim 20, wherein said therapy delivery means is a composition wherein said therapeutic agent constitutes between about 0.01% to 50% by weight of the therapy delivery means and said composition has a structural rigidity in the range of between about 50A Shore hardness and 95D Shore hardness.

24. The pacing lead of claim 1, wherein said therapeutic delivery means has at least one therapeutic eluting opening and said therapeutic delivery means further comprises a therapeutic eluting reservoir in fluid communication with said at least one therapeutic eluting opening.

25. The pacing lead of claim 24, wherein said at least one therapeutic eluting opening comprises at least one horizontal slot.

26. The pacing lead of claim 24, wherein said at least one therapeutic eluting opening comprises at least one vertical slot.

27. The pacing lead of claim 24, wherein said at least one therapeutic eluting opening comprises at least one port.

28. The pacing lead of claim 24, wherein said therapeutic delivery means further comprises means for sealing said at least one therapeutic eluting opening.

* * * * *